United States Patent [19]
Ruben

[11] Patent Number: 6,146,655
[45] Date of Patent: *Nov. 14, 2000

[54] FLEXIBLE INTRA-ORAL BANDAGE AND DRUG DELIVERY SYSTEM

[75] Inventor: Philip H. Ruben, Beverly Hills, Calif.

[73] Assignee: Softy-Flex Inc., Los Angeles, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/920,407

[22] Filed: Aug. 29, 1997

[51] Int. Cl.[7] .............. A61K 6/08; C09K 3/00; A61C 9/00; B65D 33/16
[52] U.S. Cl. ............ 424/443; 106/35; 424/445; 424/447; 424/485; 523/109; 366/3; 383/63; 383/96
[58] Field of Search .................. 424/443, 445, 424/447, 485; 106/35; 523/109

[56] References Cited

U.S. PATENT DOCUMENTS

| | | | |
|---|---|---|---|
| 4,268,497 | 5/1981 | Griffin et al. | 424/27 |
| 4,336,299 | 6/1982 | Holst et al. | 428/288 |
| 4,381,947 | 5/1983 | Pellico | 106/38.5 D |
| 4,394,172 | 7/1983 | Scheuble et al. | 106/385 D |
| 4,468,484 | 8/1984 | Pellico | 523/109 |
| 4,515,913 | 5/1985 | Pellico | 523/109 |
| 4,530,220 | 7/1985 | Nambu et al. | 62/530 |
| 4,543,372 | 9/1985 | Watanabe et al. | 523/109 |
| 4,608,088 | 8/1986 | Lokken | 106/35 |
| 4,626,558 | 12/1986 | Pellico | 523/109 |
| 4,664,630 | 5/1987 | Lokken | 433/180 |
| 5,306,337 | 4/1994 | Winkel et al. | 106/35 |
| 5,417,750 | 5/1995 | Cohen et al. | 106/35 |
| 5,543,443 | 8/1996 | Rajaiah et al. | 523/120 |
| 5,605,889 | 2/1997 | Curatolo et al. | 514/29 |
| 5,612,411 | 3/1997 | Gross | 525/54.3 |
| 5,658,586 | 8/1997 | Rajaiah et al. | 424/435 F |
| 5,676,546 | 10/1997 | Heitmann et al. | 433/199.1 |
| 5,688,923 | 11/1997 | Gerrish et al. | 536/2 F |
| 5,696,181 | 12/1997 | Chang et al. | 523/118 |
| 5,709,467 | 1/1998 | Galliano | 366/430 |

*Primary Examiner*—Shep K. Rose
*Attorney, Agent, or Firm*—Paul J. Sutton; Barry G. Magidoff

[57] ABSTRACT

A flexible intra-oral bandage and kit thereof including an hydrolyzable powder/water-wettable fiber mixture enclosed in a flexible, water-permeable, non-stick envelope. The envelope is immersed in water or medication so that the liquid is absorbed through the envelope to wet the hydrolyzable powder/water-wettable fiber mixture and form a moldable tacky gel. The envelope is then removed from the gel and the gel is manually molded and placed in a desired location in a patient's oral cavity. The kit can also be used as a drug delivery system to deliver medication to a patient through the oral cavity.

17 Claims, 5 Drawing Sheets

FLEXIBLE INTRA-ORAL BANDAGE AND DRUG DELIVERY SYSTEM

BACKGROUND OF THE INVENTION

FIELD OF THE INVENTION

The present invention relates to a flexible intra-oral bandage and drug delivery system. More specifically, the invention relates to a kit for providing a flexible intra-oral bandage capable of intra-oral adhesion and intra-oral drug delivery in a water-based system.

INTRODUCTION

The problem of providing an intra-oral bandage which will remain in place to cover and protect a sore, irritated or exposed tissue surface in the mouth has been approached in many ways. In pre-colonial America, a mixture of ground mussel shells, lime and tobacco leaves was chewed to form a putty-like substance that was placed over infected teeth and gums. Gums, resins, plant roots, animal parts and oils would also be added to this primitive mixture.

Today, there are many periodontal dressings used after periodontal and oral surgical procedures. These conventional dressings present several disadvantages. They are too complicated to be changed by a patient and therefore a skilled dentist or dental assistant must change the dressing for the patient. Dentists may also use a combination of zinc oxide and eugenol to cover an affected area.

For example, U.S. Pat. No. 2,430,740 to Sharples teaches mixing a fibrous mineral medicament with therapeutically inert fibers, such as cotton fibers, to form a therapeutic dressing. U.S. Pat. No. 5,192,802 to Rencher teaches a bioadhesive pharmaceutical carrier containing a polymer blend of sodium carboxymethyol cellulose and xanthan gum or sodium alginate for use as an oral bioadhesive pharmaceutical carrier.

U.S. Pat. No. 4,876,092 to Mizobuchi et al. teaches an adhesive preparation including an adhesive layer containing carboxyvinyl polymer, a water-insoluble methacrylic copolymer, a polyhydric alcohol and a pharmaceutically active agent, and a water-impermeable and water-insoluble carrier layer containing a plasticizer which can adhere to a patient's oral cavity. U.S. Pat. No. 4,981,875 to Leusner et al. teaches use of etofenamate for preparing compositions to treat bacterial, viral or fungicidal inflammations in a patient's oral cavity.

U.S. Pat. No. 5,242,910 to Damanj teaches use of polylactide/glycolide compositions for releasing drugs in a patient's oral cavity. U.S. Pat. No. 3,219,527 to Gurney teaches eugenol-containing periodontal dressings. U.S. Pat. No. 5,437,872 to Lee teaches a pharmaceutical tablet or lozenge comprising a non-absorbable pharmaceutically active agent combined with a tablet matrix for controlled and sustained release of the agent into a patient's mouth and gastro-intestinal tract.

U.S. Pat. No. 5,102,666 to Acharya teaches a polymeric delivery system for controlled intra-oral release of active agents, such as medicinal agents, breath fresheners and flavors. The active agent is combined with a calcium polycarbophil matrix. U.S. Pat. No. 3,996,934 to Zaffaroni teaches a bandage capable of administering controlled quantities of systemically active drugs through a patient's skin or mucosa.

U.S. Pat. No. 307,537 to Foulks teaches use of a dental bag containing capsicum to treat periodontitis.

Although such conventional surgical dressings can be mixed with medicine, such as tetracycline, the dressings are not fully water-wettable and absorptive. Therefore, only the surface of the dressing in contact with the affected area is available to deliver the medication, and even then the dressing is only able to deliver medication over a short period of time, normally only a few hours. The interior of the mouth is continuously awash in water, i.e., saliva, which has always been considered a problem when applying a covering to tissue surfaces within the mouth.

Such conventional dressings also fail to remain properly positioned in the mouth for any length of time. The inventor is unaware of any flexible, water-absorbable system capable of remaining positioned in the mouth for any length of time. The prior art has generally looked to reduce the effect of water on the dressing; even asbestos fibers have been used in an attempt to hold dental dressings in place.

In addition, most intra-oral dressings irritate healthy gum tissue surrounding the area to be treated. For example, the De Trey® Peripac periodontal pack available from Adolf Haupt & Co. of Germany is a surgical cement pack that is applied directly to an affected intra-oral area while it is soft and moldable. The dressing hardens once it comes into contact with water. The dressing must cover only the wound area and/or the periodontal area to avoid irritation of healthy tissue. In addition, acrylic crowns must be protected with a film of Vaseline to prevent the dressing from adhering to the crown.

Where a patient has sensitive teeth due to abrasion or gum erosion, a dentist will cover the abraded area with a filling or use chemical agents to seal the tooth. Alternatively, the dentist will instruct the patient to brush with a desensitizing toothpaste, such as Sensodyne®, which is available from Block Chemical Company, Inc. of Jersey City, N.J. A desensitizing toothpaste contains a chemical agent for sealing the tooth by ion replacement. Typically, the patient is instructed to brush with the toothpaste for 2 to 3 minutes twice a day. Thus, the chemical agent in the toothpaste comes in contact with the sensitive teeth for, at most, 4 to 6 minutes a day.

It is also well known to use an alginate gel as a dental impression material. A water-soluble alginate salt, such as sodium or potassium alginate, is reacted in water with a calcium or lead salt to form a water-insoluble gel dental impression material.

There is a need to provide a flexible intra-oral bandage capable of delivering medication in a water-washed environment over an extended period of time, which remains securely in place in a patient's mouth, will not irritate surrounding healthy gum and mouth tissue and can be easily changed by the patient.

Therefore, it is an objective of the present invention to provide a flexible intra-oral bandage which remains securely in place in a patient's mouth without irritating surrounding tissue, and a kit for such an intra-oral bandage.

It is another objective of the present invention to provide a flexible intra-oral bandage and kit therefor capable of delivering medication in a water-washed environment for an extended period of time while remaining securely in place in a patient's mouth without irritating surrounding tissue.

It is a further objective of the present invention to provide an intra-oral drug delivery system capable of delivering medication in a water-washed environment for an extended period of time while remaining securely in place in a patient's mouth without irritating surrounding tissue.

SUMMARY OF THE INVENTION

The present invention provides a flexible intra-oral bandage which remains securely in place in a patient's mouth without irritating surrounding tissue. The bandage comprises a flexible, cohesive hydrolyzed gel/water-wettable, fiber-reinforced material. The invention also provides a kit for making the bandage, comprising a hydrolyzable powder/water-wettable fiber mixture enclosed in a flexible, water-permeable, non-stick envelope that does not adhere to the hydrolyzed gel/fiber product after wetting with an aqueous liquid. The hydrolyzable powder is preferably a water-soluble alginate salt, commonly used for forming dental impressions mixed with another salt which forms a water-insoluble alginate gel in water. The envelope is preferably a non-woven water-permeable fabric. Preferably, the hydrolyzable powder/water-wettable fiber mixture and water-permeable envelope kit is wrapped in a package having a non-adherent surface, such as a package formed of perforated aluminum foil and Mylar film. The package may also be water-permeable.

To activate the bandage, the powder/water-wettable fiber mixture enclosed in the water-permeable envelope is immersed in an aqueous liquid, such as water. Alternatively, where the outer package is water-permeable, the water-permeable package containing the hydrolyzable powder/water-wettable fiber mixture enclosed in the envelope is soaked in the aqueous liquid. The water-permeable envelope (and the water-permeable package) allows the liquid to pass through to the hydrolyzable powder-water wettable fiber mixture to wet the mixture and convert it to a moldable tacky fiber-reinforced gel. The envelope also serves to retain the alginate powder-water wettable fiber mixture while immersed in any aqueous liquid.

Although it is preferred that the "hydrolyzable powder" is particulate, i.e., non-fibrous, in nature, having a particle size relatively substantially smaller than the length of the wettable fibers, the powder can include short, fibrous, hydrolyzable particles, preferably which are much shorter in length than the wettable fibers.

The wettable fibers have an individual length of at least 3 mm, and preferably in the range of from about 2 mm to about 4 mm, to obtain the desired reinforcement effect. There should be at least one order of magnitude difference between the diameter and length of the wettable fibers. The fibers can be provided loose or by way of a preformed tissue sheet.

After the kit is removed from the liquid, the tacky fiber-reinforced gel is removed from the package and envelope, and manually molded and positioned in place over a desired tissue surface in a patient's oral cavity.

The present invention also provides a flexible intra-oral bandage and kit therefor capable of delivering medication in a water-washed environment for an extended period of time while remaining securely in place in a patient's mouth without irritating surrounding tissue. In this embodiment, the aqueous liquid in which the flexible intra-oral bandage described above is immersed comprises a solution of a liquid medication or a solid medication dissolved in water. The medication is absorbed in the bandage and the bandage is placed in the patient's mouth, as discussed above. This allows the medication to be continuously delivered to the patient through the oral cavity. The term "absorbed" is not to be limited to absorption into the interior of the fibers or the gel, but is inclusive of an external adsorption, or even coating on the fibers of the medication, or an aqueous solution thereof. Alternatively, granular medication can be dispersed in the powder/fiber mixture.

The present invention further provides an intra-oral drug delivery system capable of delivering medication in a water-washed environment for an extended period of time while remaining securely in place in a patient's mouth without irritating surrounding tissue.

DETAILED DESCRIPTION OF THE PREFERRED EMBODIMENTS

Figure 1A:
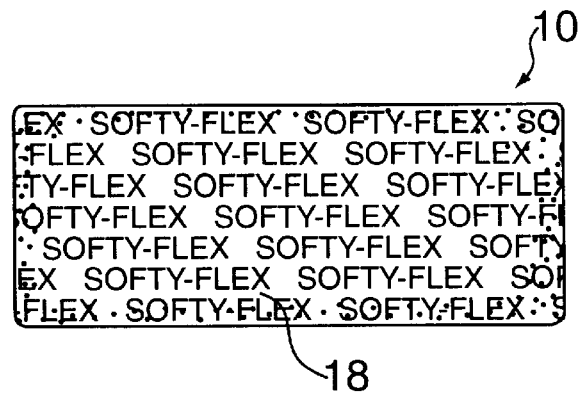
FIG. 1A is a top view of the bandage kit of this invention wrapped in a protective package.
Figure 1B:
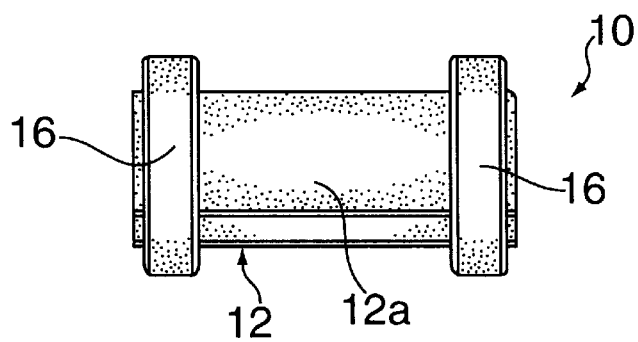
FIG. 1B is a top plan view of the unwrapped bandage kit.

In describing preferred embodiments of the present invention illustrated in the drawings, specific terminology is employed for the sake of clarity. However, the invention is not intended to be limited to the specific terminology or to the illustrated examples so selected, and it is to be understood that each specific element includes all equivalents which operate in a similar manner to accomplish a similar purpose.

As illustrated in FIGS. 1A through 1G, this invention provides a kit 10 for an intra-oral bandage, the kit comprises a powder/water-wettable fiber mixture 20 enclosed in a flexible, water-permeable, non-stick envelope 12. The powder/water-wettable fiber mixture 20 is preferably comprised of a polysaccharide powder, such as an alginate powder, mixed with water-wettable fibers, such as cellulose fibers. Preferably, the powder/water-wettable fiber mixture contains from about 60 to about 70 weight percent powder and from about 20 to about 40 weight percent fibers, e.g., cellulose fibers, more preferably, about 65 weight percent alginate powder and from about 30 to about 35 weight percent wettable, e.g., cotton fibers.

In an alternative embodiment of this invention, at least a major portion of the loose fibers is replaced by a fiber sheet, which can enclose the loose hydrolyzable particle mixture. The fiber sheet can be formed from cellulose fibers, or other fibers which are water-wettable, including cotton or wood pulp fibers, which have little or no binder material, but are self-coherent. Alternatively, a water-soluble binder, such as is used in toilet tissue, can be present.

In this embodiment, the water-hydrolyzable powder is spread over the fiber sheet, which is then folded over the powder, and the folded fiber sheet placed within the matrix envelope. The powder can be only particulate material, or can contain a relatively small proportion, e.g., preferably not more than about 34% by weight of the powder, of a fibrous material. The fiber sheet must be one which disintegrates when wetted, to provide the fibers for reinforcing the dental bandage of this invention. The shape of the fiber sheet is retained in the final hydrolyzed mixture, and that wetted sheet can be placed in the mouth as a more neat bandage, without requiring manual molding. It may be desirable, and most preferred, to further fold the wetted tissue sheet lengthwise, after removal from the matrix envelope.

The hydrolyzable powder is preferably comprised of sodium or potassium alginate and a soluble salt reactor, which forms an insoluble alginate salt, such as calcium sulfate, or even a lead-based salt, e.g., lead silicate. The powder preferably also contains an absorbent filler, such as diatomaceous earth, and a setting retarder, such as sodium or potassium phosphates, oxalates or carbonates. These alginates are commercially available under the brand names, e.g., COE Alginate, D-P Key, Opotow Jelset, and Supergel.

The activity of alginate impression medium is well known to the dental art, and need not be more fully disclosed herein. Other useful gel materials include soluble vinyl and silane polymers.

For purposes of the present invention, the addition of a non-hydrolyzable polysaccharide, such as corn starch, improves the initial handling of this mixture when molding and applying it to the oral surfaces.

A useful composition of a hydrolyzable powder is as follows:
  about 12 weight percent sodium or potassium alginate;
  about 12 weight percent of a reactor salt, such as calcium sulfate hemihydrate;
  about 70 weight percent diatomaceous earth;
  about 2 weight percent tri-sodium phosphate; and
  about 1 weight percent corn starch.

Another example of a composition of the hydrolyzable powder/water-wettable fiber mixture 20 is as follows:
  about 8 weight percent sodium or potassium alginate;
  about 8 weight percent calcium sulfate;
  about 47 weight percent diatomaceous earth;
  about 1 weight percent tri-sodium phosphate;
  about 1 percent corn starch; and
  about 30 weight percent cotton fiber.

Other wettable reinforcing fibers include natural cellulosic fibers, such as flax, hemp or jute, or wood fibers, or synthetic fibers, such as rayon.

The hydrolyzable powder may also contain coloring agents (natural or artificial), natural or artificial flavoring agents, fluoride salt, zinc oxide or magnesium oxide and calcium sulfate. Preferred coloring materials of a type normally used for dental packing include Butler Color, such as Butler, G.U.M., Red-Cote, and D & C Red # 28, 1.5%, from the John O. Butler Company, Chicago, Ill.

Flavor additives useful in this context include any desired international flavor, which is preferably added with the liquid.

Medicaments that can usefully be delivered by the present invention include the following, by way of example.

Fluoride salt, for example, sodium fluoride, to act as a tooth enamel hardener, preferably not more than about 1 weight percent fluoride salt is added with the aqueous solution.

Zinc oxide or magnesium oxide are also generally added to the hydrolyzable powder, such as in the commercially available alginate dental impression materials. These compounds, it is believed, have an impact on the setting speed, and zinc oxide, at least, has soothing effects on sore tissue. Generally, not more than about 2% by weight of zinc oxide and magnesium oxide is present.

The fibers contained in the powder/water-wettable fiber mixture must be fully wettable and water absorptive, and include, preferably, cellulosic or cellulose derivatives, such as cotton or flax. The fibers are most preferably cotton fibers, at least 3 mm in length. Other fibers useful herein include flax, jute, hemp or rayon.

Preferably, before mixing, the powder particles and fibers are each electrically charged with opposite charges. For example, the polysaccharide powder particles can be positively charged and the fibers negatively charged. This prevents clumping together of like particles, and enhances close mixing of different particles, e.g., the positively charged hydrolyzable powder particles will be attached to, and completely cover, the negatively charged wettable fibers.

The powder and fibers are each preferably electrically charged prior to enclosure within the envelope to achieve maximum saturation of the powder, e.g., alginate, on the wettable, e.g., cotton, fibers. The charges can be applied to the powder particles and fibers by known means, such as a mixing container with charged plates.

Once the powder/water-wettable fiber mixture 20 comes in contact with the aqueous liquid, the charges become neutralized as the alginate is hydrolyzed by the aqueous liquid and reacts with the, e.g., calcium salt, to form a moldable tacky gel having cross-linked structure created by the calcium ion. Once the alginate is hydrolyzed, the fibers provide reinforcement when molding the gelled alginate into a desired shape.

The flexible, non-stick, water-permeable envelope 12 is formed of a material having an outer surface 12a which, when immersed in an aqueous liquid, will absorb and pass the liquid so that the liquid will come into contact with the powder/water-wettable fiber mixture; the envelope also has a smooth non-adherent inner surface 12b that will not adhere to the wetted powder/water-wettable fiber mixture 20 after mixing is completed, but the envelope will hold the powder/water-wettable fiber mixture in place during mixing. The envelope is preferably formed of a non-woven fabric, such as the type used in medical and filtration applications. One example of such a fabric is Stratix, a non-woven polyolefin fabric, made of high density polyethylene and/or polypropylene fibers, manufactured by Delnet Applied Extrusion Technologies, Inc., of Middletown, Del.

The envelope fabric acts as a matrix for the powder/water-wettable fiber mixture when it is wetted, helping to form the oral patch. It preferably comprises a soft, absorptive material which will quickly absorb and pass through an aqueous liquid, so that the powder/water-wettable fiber particles immediately come into contact with, and are activated by, the liquid, and the mixture remains uniform. The envelope fabric also acts as a one-way valve, allowing liquid in but preventing the hydrolyzable powder or the fibers from dispersing out of the envelope into the body of liquid. In addition, envelope 12 also serves to hold the powder/water-wettable fiber mixture firmly in place so it is not altered during handling, shipping or storage. The Delnet Stratix sheet material is especially effective, because of the distinctive properties of the two major surfaces. One side of the sheet, which would form the outside surface of the envelope in the Kit of this invention, is designed for maximum absorption and passage of an aqueous liquid to the inside surface, and the second (inside) surface is non-adherent and very smooth, thus highly useful to enclose the bandage while it is being wetted, and to permit easy removal of the gelled bandage when the envelope is opened.

Preferably, the powder/water-wettable fiber mixture 20 is sealed within the envelope 12 by sealing means, such as adhesive tape 16, until it is desired to be used.

Figure 1C:
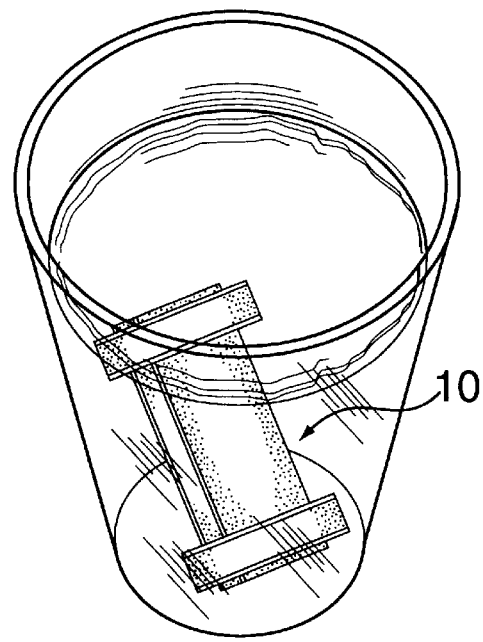
FIG. 1C is a perspective view showing the bandage kit immersed in a liquid.
Figure 1D:
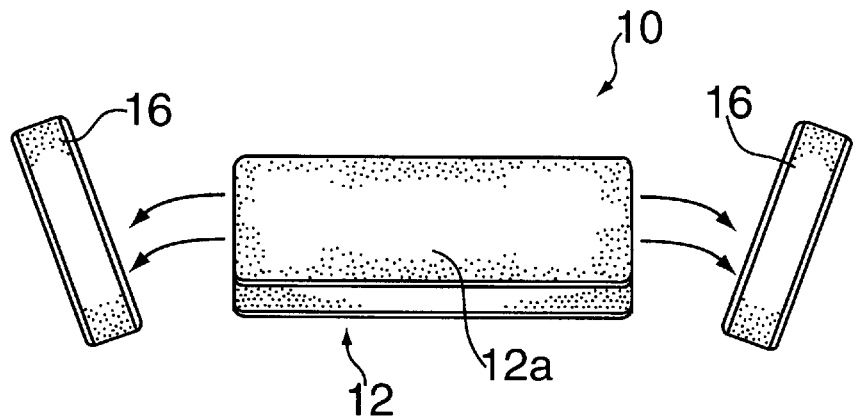
FIG. 1D is an exploded view of the unwrapped bandage kit.
Figure 1E:
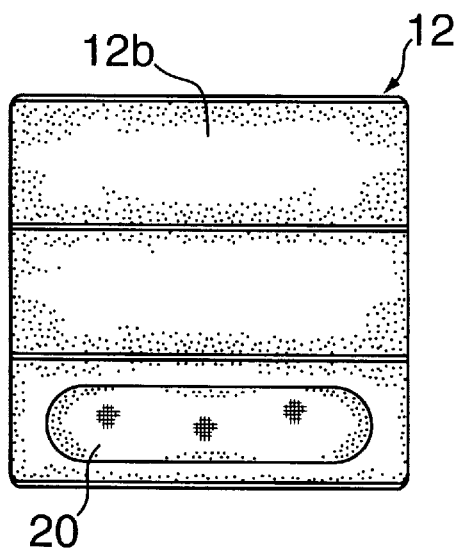
FIG. 1E is a top plan view showing the wetted hydrolyzable powder/water-wettable fiber mixture on the opened envelope ready for removal.
Figure 1F:
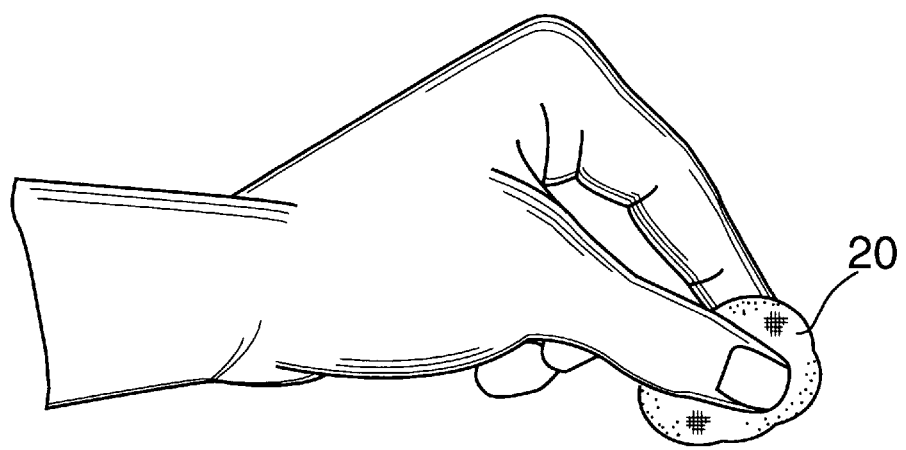
FIG. 1F is a side view showing manual molding of the wetted alginate powder/water-wettable fiber mixture.
Figure 1G:
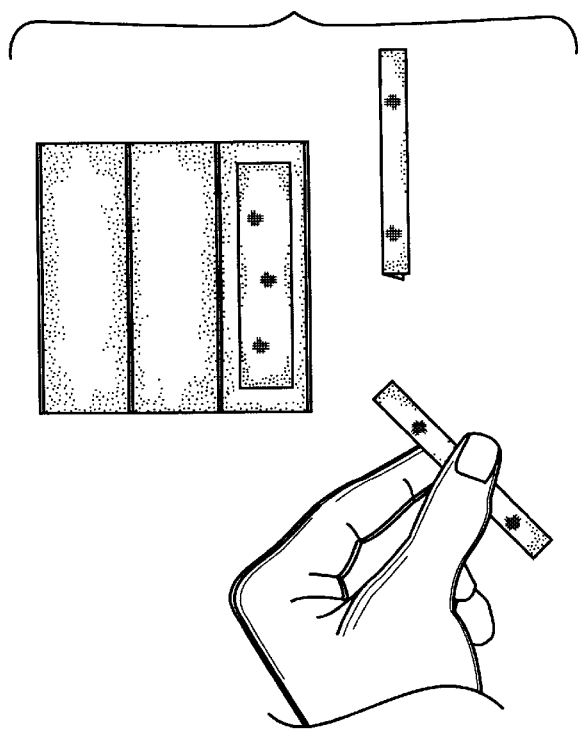
FIG. 1G is a top plan view of another embodiment where the fibers are provided by a tissue sheet.
Figure 1H:
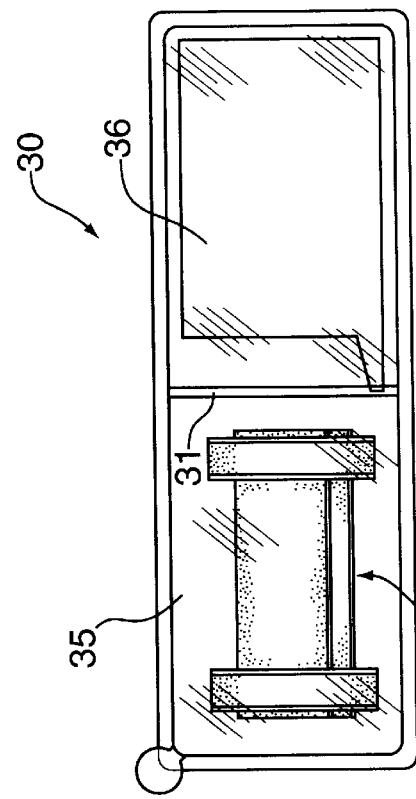
FIG. 1H is another embodiment where the bandage kit and a pre-measured aliquot of a desirable aqueous liquid, containing a desired medication, are packaged in a two-compartment package.

The bandage kit 10 is preferably wrapped in an outer protective package 18. The package may be formed of any suitable material, such as aluminum foil, Mylar film, poly-coated paper, Delnet film, waxed paper, and all non-porous materials. Alternatively, the outer package may be perforated to allow passage of liquid through the package, and in turn through the envelope to the powder/water-wettable fiber mixture. Alternatively, as shown in FIG. 1H, bandage kit 10 may be packaged in a two-compartment container 30, wherein the compartments are separated by a watertight breakable barrier 31, with one compartment 35 containing bandage kit 10 and the other compartment 36 containing a premeasured aliquot of an aqueous liquid and, if desired, a dissolved medication. The user merely breaks the frangible wall 31 between the two compartments to mix the bandage with the liquid and hydrolyze the powder/water-wettable fiber mixture.

Bandage kit 10 is used as follows. First, bandage kit 10 is removed from the outer package 18 and is immersed in water or another aqueous liquid, as illustrated in FIG. 1C. Alternatively, if the outer package 18 is sufficiently permeable to allow passage of liquid through package 18 to envelope 12, then the entire package containing the bandage kit 10 may be immersed in the liquid. Preferably, the temperature of the liquid is between 10° C. and 25° C., and more preferably between about 15° C. and 20° C. For ease of use, mixing can take place at room temperature. Alternatively, the liquid may be cooled, for example, by refrigeration, or by adding a piece of ice to the liquid to reach the desired temperature.

The aqueous liquid can be water or any aqueous solution or suspension, such as an aqueous medication or a suspension of medication. For example, where the user would like to use a bandage kit 10 to apply medication to an affected area of the mouth, the liquid may comprise a medicated mouth wash, such as Peridex®, available from Proctor & Gamble of Cincinnati, Ohio, or Perioguard®, available from Colgate Oral Pharmaceutical, of Canton, Mass. Other suitable liquids include aqueous solutions containing a water-soluble desensitizing agent or anti-caries agents, such as fluoride salts(sodium fluoride or stannous fluoride), potassium oxylate (available from John O. Butler Company, of Chicago, Ill.) or strontium chloride, or any other such water-soluble agent.

Alternatively, where the user would like to use the bandage kit 10 to deliver a systemic medication orally, the aqueous liquid may contain a systemic medication, such as an antibiotic or a hormone, or any time-released drug, such as, for example, antibiotics, vaccines, topical anesthetics, breath fresheners, vitamins, homeopathic drugs, or appetite suppressers. Time release granules for a desired medication, if mixed into the powder, will be dispersed into and through the hydrolized gel. The granules would then be gradually dissolved by the saliva when the bandage is placed in the mouth.

Bandage kit 10 is preferably immersed in the aqueous liquid for at least about 10 to 30 seconds; more preferably not longer than about 15 to 20 seconds is necessary, and in most cases, not more than about 15 seconds. Longer immersion times may be needed when a tissue sheet of fibers is used. The viscosity of the aqueous liquid, if unusually high because of the additive dispersed and the temperature, may require longer soaking periods. Generally, the kit is immersed in excess liquid.

Once bandage kit 10 has been fully soaked with the liquid, the envelope is removed from the liquid, the seals (adhesive tapes 16) are removed from envelope 12, and envelope 12 is unwrapped to expose the moldable, fully wetted powder/water-wettable fiber mixture 20. The user then removes powder/water-wettable fiber mixture 20 from envelope 12, manually molds the powder/water-wettable fiber mixture 20 as shown in FIG. 1F to form a bandage of the desired shape, or folds the wetted tissue 40 (as shown in FIG. 1G), places the wetted bandage 20 in a desired location in his or her mouth, and secures the bandage 20 to the desired location by applying light manual pressure to the gelled bandage 20, causing it to adhere to the tissue surface.

Figure 2A:
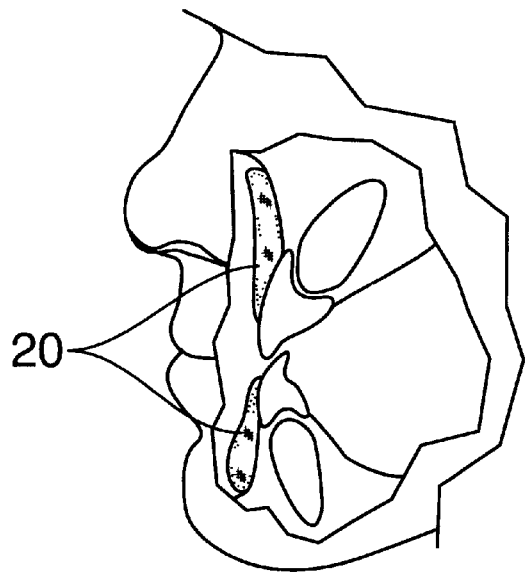
FIG. 2A is a side view showing placement of the molded bandage in the vestibule of a patient's mouth.
Figure 2B:
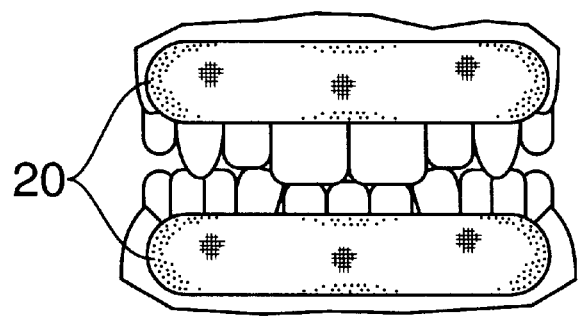
FIG. 2B is a front view showing placement of the molded bandage over a patient's upper and lower gums.
Figure 2C:
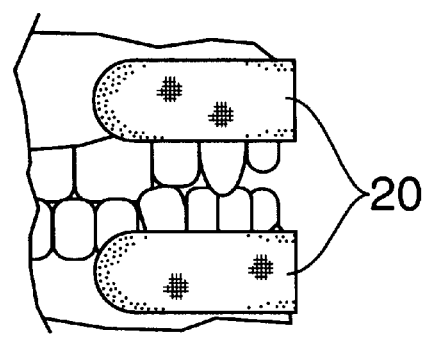
FIG. 2C is a side view showing placement of the molded bandage over a patient's upper and lower gums.
Figure 2D:
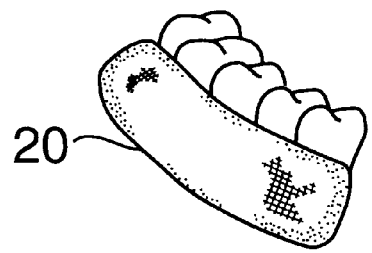
FIG. 2D is a side view showing placement of the molded bandage over a patient's lower gums.
Figure 2E:
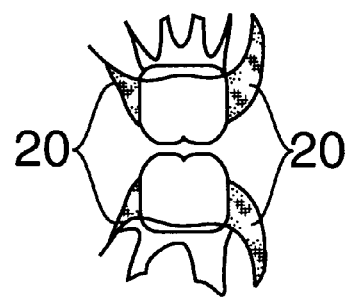
FIG. 2E is a side view showing placement of the molded bandage on either side of a patient's upper molars and on either side of a patient's lower molars.
Figure 2F:
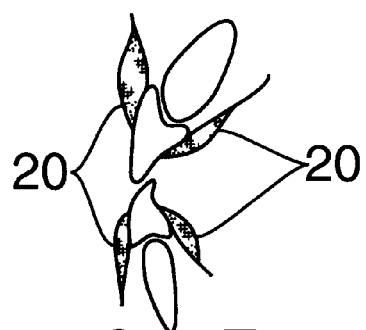
FIG. 2F is a side view showing placement of the molded bandage on either side of a patient's upper front teeth and on either side of a patient's lower front teeth.

As illustrated in FIGS. 2A through 2F, the molded powder/water-wettable fiber mixture 20 can be placed in any location in a user's mouth. For example and without limitation, FIG. 2A illustrates placement of the powder/water-wettable fiber mixture 20 in the upper and lower vestibules 26, 28 of a user's mouth. FIG. 2B illustrates placement of the molded powder/water-wettable fiber mixture 20 on a user's front upper and front lower outer gums, and FIGS. 2C and 2D are side views illustrating placement of the molded powder/water-wettable fiber mixture 20 on a user's side upper and side lower outer gums. FIGS. 2E and 2F are side views illustrating placement of powder/water-wettable fiber mixture 20 on the inner and outer surfaces of a patient's upper and lower gums.

The pliable hydrous gel can be molded, merely by manual pressure, to accurately conform to any surface of a patient's teeth and/or periodontal tissue, taking on the shape of that part of the patient's mouth and extending into the inner proximal area of the teeth so that, once positioned, the molded gelled fiber mixture will remain in place. In addition, surface tension between the surface molecules of the bandage material (such as a hydrolyzed alginate/cotton fiber bandage), and the gingival tissue and teeth, as well as pressure differentiation between the oral tissue and the wet alginate, prevent dislodgment of the molded gel/fiber bandage 20. The outer surface of the molded gel/fiber mixture bandage 20 will be made smooth through contact with the patient's cheek or tongue, and the molded powder/water-wettable fiber mixture will not irritate surrounding healthy tissue, nor the tissue to which it is adhered.

Thus, the bandage and bandage kit have many possible uses, including but not limited to: forming a protective barrier over an area of a patient's mouth, in particular a sensitive area, a tissue graft area, an area that has undergone periodontal surgery or oral surgery, as a prevention and/or treatment for "dry socket," due to tooth removal, or for pericoronitis flap infection, around the eruption of a patient's third molars (wisdom teeth).

The bandage is capable of holding a molded shape and is non-irritating to surrounding tissue. In addition, the gelled fiber mixture (bandage) 20 is bio-degradable and harmless if accidentally chewed or swallowed. It will not damage acrylic crowns or other dental fixtures, and is easily removed by being peeled away without tearing or leaving a residue.

The bandage and bandage kit of this invention also provide a water-based intra-oral drug delivery system and method for delivering either topical treatments to an affected inter-oral area, or for systemic delivery of medication through tissue absorption and dispersion by the patient's saliva.

First, the bandage kit provides a water-based drug delivery system and method for delivering topical treatments to an affected intra-oral area. For example, the bandage kit can be used to deliver desensitizing medication to sensitive teeth. One example is the delivering of desensitizing medication to sensitive teeth using the delivery system of the present invention; by mixing a small amount of the active ingredient in a desensitizing toothpaste or gel, such as Sensodyne®. For example, approximately 1 to 3 inches of the Sensodyne® paste or gel can be mixed in enough water to form a slurry. The active ingredient will dissolve in the water. Next, the bandage 10 is immersed in the slurry for about 15 seconds, so that the liquid is absorbed through the envelope 12 to wet and to activate the powder/water-wettable fiber mixture 20. The wetted, gelled powder/water-wettable fiber mixture 20 is then removed from the envelope, molded, and applied to the sensitive area as described above. The desensitizing agent which was also dispersed throughout the gelled bandage with the liquid is thus delivered, at a substantially constant rate, to the patient's sensitive teeth for a relatively extended period of time, e.g., up to about 12 hours.

The oral bandage of this invention also provides a drug delivery system and method for systemic delivery of various medications to a patient through (1) oral tissue absorption of medication and (2) saliva dispersion of medication. Many systemic aqueously-dispersible medications, including, but not limited to antibiotics, can be presented with this system.

The medication should be provided in an aqueous liquid dispersion, preferably a solution, so that it can be passed through the surface of the envelope 12 to the powder/water-wettable fiber mixture 20, as described in detail above. The oral bandage kit of this invention thus provides a water-based delivery system which allows continuous oral administration of medication; it is believed that the delivery is based upon osmotic action, but the precise mechanism is not specifically defined. Similarly, when the terms "hydrolyzing," or "hydrolyzable," and "gel" are used, it is not intended to limit this invention to any particular chemical reaction or products; these terms merely provide a short-hand expression for the action of the aqueous liquid and any reactor salt on the powder and fiber, and the appearance of the wetted powder/fiber bandage material.

When the water-activated powder is an alginate gel, which is a water-based material, there is believed to be an osmotic effect which causes the medication absorbed by the powder/water-wettable fiber envelope to be dissolved by the saliva and to diffuse through the bandage into the mouth. The topical material can then be absorbed through the oral tissue to which the bandage is adhered, and/or the medication can be swallowed with the saliva. The gelled-fiber bandage can form an osmotic membrane. In addition, the smooth wet surface of the gelled fiber bandage against the oral tissue creates a surface tension differential with the mouth surface tissue and aids in the adherence of the bandage to the mouth surface.

The user will preferably change the bandage at least once every 12 hours, more preferably at least once every 8 hours, and most preferably, at least once every 12 hours. The required bandage changing time may vary with the type of medication to be delivered through the bandage and the condition of the tissue. For example, 10 minutes for a topical anesthetic application to sound tissue.

Other modifications and variations of the above-described embodiments of the present invention are possible, as appreciated by those skilled in the art in light of the above teachings.

It is therefore to be understood that, within the scope of the appended claims and their equivalents, the invention may be practiced otherwise than as specifically described.

What is claimed is:

1. A kit for preparing a flexible intra-oral bandage, the kit comprising a water-permeable envelope, the envelope being formed of a non-woven, water-porous fabric, a powder/fiber mixture contained within the envelope, the powder/fiber mixture comprising a dry, particulate water-soluble powder, comprising a soluble alginate salt admixed with a soluble reactor salt, and water-wettable fibers, the reactor salt and alginate being present in relative quantities sufficient to produce, when admixed with water, a water-insoluble cross-linked alginate salt, said fibers carrying a static electricity charge, the thickness of the fiber being an order of magnitude smaller than the length of the fiber, and the powder carrying a static electricity charge opposite to that of the fibers, and having a particle size smaller than that of the fibers; the charged powder particles being distributed on and adhering to the oppositely charged fibers; said porous envelope being so arranged to allow an aqueous liquid to pass through to and to wet said alginate-salt powder/fiber mixture when the envelope is immersed in water, and the powder/fiber mixture being so admixed that when wetted with water it is converted to a moldable, tacky fiber-reinforced gel, suitable for use as an intra-oral bandage.

2. The kit of claim 1, wherein the hydrolyzable particulate material comprises a soluble alginate salt and a reactor salt, the alginate salt and the reactor salt being reactable in an aqueous liquid to form a moldable gel comprising a water-insoluble alginate salt.

3. The kit of claim 1, wherein the hydrolyzable particulate material comprises an alkali metal alginate salt and a water-soluble calcium salt.

4. A method of forming an intra-oral bandage, for covering exposed tissue surface in the oral cavity of a patient, the method comprising the steps of mixing an aqueous liquid with a dry mixture, the dry mixture comprising a water-wettable fibrous material, and a particulate hydrolyzable gel-forming material, the water wettable fibrous material being selected from loose fibers and a fiber sheet which is adapted to disintegrate into loose fibers when immersed in an aqueous liquid, the gel-forming material comprising a soluble alkali metal alginate salt and a reagant salt which are designed to react together to produce a water-insoluble alginate gel when wetted with water; thus forming a fiber-containing, water-insoluble alginate gel mixture wherein the fiber is dispersed throughout the gel; manually molding said fiber-containing gel to a selected shape wherein the fiber serves to reinforce the structure of the gel; and applying said molded, fiber-reinforced gel over said exposed tissue surface in the oral cavity, the fiber-reinforced gel being non-adhesive with the tissue or with the teeth.

5. A kit for preparing a flexible intra-oral bandage, in accordance with claim 1, the kit comprising in addition, an outer package having sides perforated so as to permit the passage of aqueous liquids into the interior of the outer package.

6. The method in accordance with claim 4 wherein said powder/fiber mixture also includes a medicament.

7. A method in accordance with claim 4 wherein said aqueous liquid also comprises a medicament.

8. The method of claim 4, further comprising providing an envelope for the water-wettable fibrous material and particulate, hydrolyzable, gel-forming material, the envelope being permeable to aqueous liquids and having an inner surface nonadherent to the insoluble gel, and wherein the aqueous liquid is infused through the envelope and into the powder/fiber mixture, so as to form the fiber-reinforced water-insoluble gel mass.

9. A kit in accordance with claim 1, and further comprising a water-tight container having a first and a second compartment, a frangible wall interposed between said compartments, said envelope being disposed in one said compartment and an aqueous liquid being disposed in the other said compartment.

10. A kit in accordance with claim 9, wherein said aqueous liquid is communicated to said envelope responsive to the rupture of said frangible wall.

11. A kit in accordance with claim 1 wherein said powder/fiber mixture includes a medicament.

12. In accordance with claim 1, wherein said envelope is encapsulated in a sealed water-impervious pouch.

13. The method in accordance with claim 4 wherein said fibrous material is selected from the group consisting of unstructured fibers and water-disintegrable tissue structures.

14. The kit of claim 1 wherein the alginate salt is an alkali metal alginate salt and the reagant salt is a soluble calcium salt, and said envelope comprising a water pervious exterior surface and a smooth, water-pervious internal surface substantially non-adherent to said hydrolyzed mixture.

15. The method of claim 8, wherein the envelope comprises a water-pervious exterior surface and a smooth water-pervious interior surface, the interior surface serving as a matrix for the formation of a flat bandage.

16. A kit for preparing a flexible intra-oral bandage, the kit comprising a water-permeable envelope, the envelope being formed of a non-woven, water-porous fabric, and a powder/fiber mixture contained within the envelope, the powder/fiber mixture comprising a dry, particulate water-soluble powder, comprising a soluble alginate powder admixed with a dry soluble calcium sulfate powder, and water-wettable fibers, the water wettable fibrous material being selected from loose fibers and a fiber sheet which is adapted to disintegrate into loose fibers when immersed in an aqueous liquid, the calcium sulfate and soluble alginate being present in relative quantities sufficient to produce, when admixed with water, a water-insoluble cross-linked calcium alginate salt, said powder/fiber mixture containing from about 60 to about 70 percent powder and from about 30 to about 40 percent fiber, said fibers having a static electricity charge and being from about 2 to about 4 millimeters in length, the thickness of the fiber being an order of magnitude smaller than the length of the fiber, and the powder having a static electricity charge opposite to the charge on the fibers and having a particle size smaller than that of the fibers; the charged powder particles being distributed on and adhering to the oppositely charged fibers; said porous inner envelope being so arranged to allow an aqueous liquid to pass through to and to wet said alginate-salt powder/fiber mixture when immersed in water, and the powder/fiber mixture being so admixed that when wetted with water it is converted to a moldable, tacky, reinforced gel, suitable for use as an intra-oral bandage.

17. The kit of claim 16, further comprising a perforated outer package, containing the water-permeable envelope, and formed of otherwise nonpermeable material, the perforations of said package and said porous inner envelope being so arranged to allow an aqueous liquid to pass through to and to wet said alginate-salt powder/fiber mixture when the package is immersed in water.

\* \* \* \* \*